United States Patent [19]

Das

[11] Patent Number: 4,611,005

[45] Date of Patent: Sep. 9, 1986

[54] 5,6-EPOXY-7-OXABICYCLOHEPTANE SUBSTITUTED PROSTAGLANDIN ANALOGS USEFUL IN THE TREATMENT OF THROMBOTIC DISEASE

[75] Inventor: Jagabandhu Das, Plainsboro, N.J.

[73] Assignee: E. R. Squibb & Sons, Inc., Princeton, N.J.

[21] Appl. No.: 736,628

[22] Filed: May 21, 1985

[51] Int. Cl.[4] ............ A61K 31/335; A61K 31/557; C07D 307/00
[52] U.S. Cl. .................................... 514/468; 549/459
[58] Field of Search .................... 549/459; 514/468

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292  8/1982  European Pat. Off. .
2039909  8/1980  United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

5,6-Epoxy-7-oxabicycloheptane substituted prostaglandin analogs are provided having the structural formula

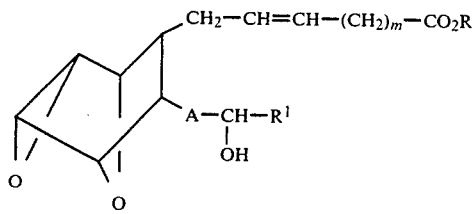

wherein m is 1 to 5, R is H, lower alkyl, alkali metal or polyhydroxylamine, and $R^1$ is lower alkyl, aryl, aralkyl, cycloalkyl, cycloalkylalkyl or lower alkenyl, including all stereoisomers thereof.

The compounds are cardiovascular agents useful, for example, in the treatment of thrombotic disease.

20 Claims, No Drawings

5,6-EPOXY-7-OXABICYCLOHEPTANE SUBSTITUTED PROSTAGLANDIN ANALOGS USEFUL IN THE TREATMENT OF THROMBOTIC DISEASE

DESCRIPTION OF THE INVENTION

The present invention relates to 5,6-epoxy-7-oxabicycloheptane substituted prostaglandin analogs which are cardiovascular agents useful, for example, in the treatment of thrombotic disease. These compounds have the structural formula

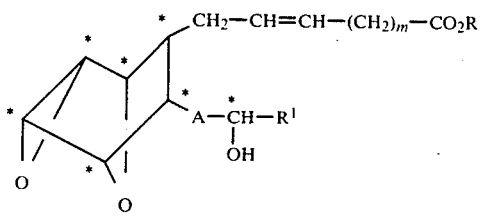

and including all stereoisomers thereof, wherein m is 1 to 5; R is hydrogen, lower alkyl, alkali metal salt or polyhydroxylamine salt; A is —CH=CH— or —(CH$_2$)$_2$—; and R$_1$ is lower alkyl, aryl, aralkyl, cycloalkyl, cycloalkylalkyl or lower alkenyl.

The present invention also includes intermediates for preparing the above compounds of the invention which have the structure

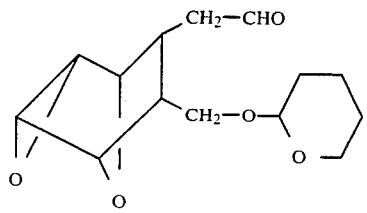

and

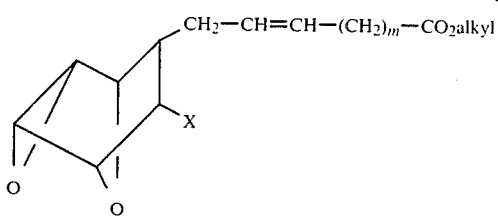

wherein X is

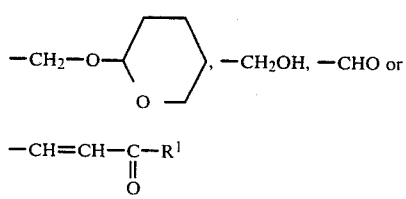

wherein m and R$^1$ are as defined above.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkyl-aryl substituent, a haloaryl substituent, a cycloalkyl substituent, an alkylcycloalkyl substituent, hydroxy, an alkylamino substituent, a nitro substituent, an amino substituent, a cyano substituent, a thiol substituent or an alkylthio substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups, an aryl group, 1 or 2 hydroxy groups, 1 or 2 alkylamino groups, 1 or 2 amino groups, 1 or 2 nitro groups, 1 or 2 cyano groups, 1 or 2 thiol groups or 1 or 2 alkylthio groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), an aryl group, 1 or 2 lower alkoxy groups, 1 or 2 hydroxy groups, 1 or 2 alkylamino groups, 1 or 2 amino groups, 1 or 2 nitro groups, 1 or 2 cyano groups, 1 or 2 thiol groups or 1 or 2 alkylthio groups.

The term "aralkyl", "aryl-alkyl" or "aryl-lower alkyl" as used herein by itself or as part of another group refers to lower alkyl groups as discussed above having an aryl substituent, such as benzyl.

The term "lower alkenyl" or "alkenyl" includes straight or branched chain radicals of from 2 to 12 carbons, preferably 2 to 6 carbons in the normal chain, which include one double bond in the normal chain, such as ethenyl, 2-propenyl, 3-butenyl, 2-butenyl, 1-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The term "polyhydroxylamine" refers to glucamine salt, tri(hydroxymethyl)aminomethane salt and the like.

The term "(CH$_2$)$_m$" includes a straight or branched chain radicals having from 1 to 5 carbons in the normal chain and may contain one or more lower alkyl or halo substituents. Examples of (CH$_2$)$_m$ groups include

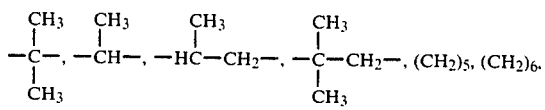

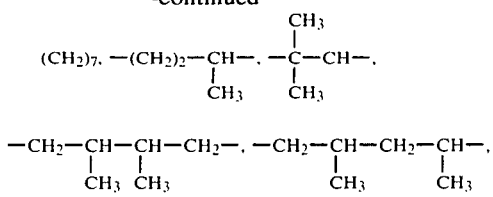

and the like.

Preferred are those compounds of formula I wherein A is CH=CH, and m is 2 or 4, R is H, and R¹ is lower alkyl, aryl, such as phenyl, or aralkyl such as benzyl, or benzyl-1-methyl or cycloalkyl, such as cyclohexyl.

The various compounds of the invention may be prepared as outlined below.

The compounds of formula I of the invention may be prepared as described below.

The starting compounds of the invention II may be prepared as follows.

Dione-A having the structure

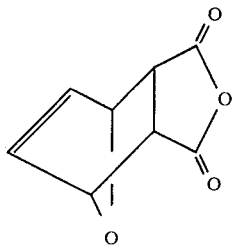

that is, 7-oxabicyclo [2.2.1]-5-heptene-2,3-dicarboxylic anhydride [Ber. 62, 554 (1929); Ann. 460, 98 (1928)], is reduced, for example, by reacting with lithium aluminum hydride or diisobutyl aluminum hydride in the presence of an inert organic solvent such as tetrahydrofuran, ether or toluene at reduced temperatures of from about −78° C. to about 67° C. to form diol B of the structure

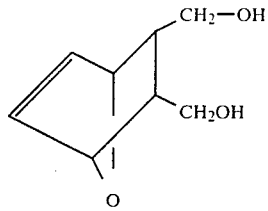

The diol B is subjected to a chloroformylation reaction by reacting B dissolved in an inert organic solvent as described above, with phosgene in the presence of a solvent such as tetrahydrofuran, toluene, benzene or xylene, to form an alcohol of the structure

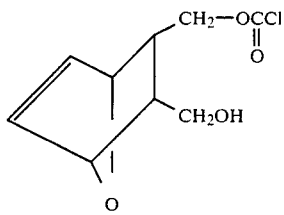

The alcohol C is dissolved in an inert organic solvent such as methylene chloride, tetrahydrofuran or ether and then reacted with an organic base, such as pyridine, triethylamine, N,N-dimethylaminopyridine or diazabicycloundecane (DBU) at reduced temperatures of from about −78° C. to about 25° C., to form cyclic carbonate D

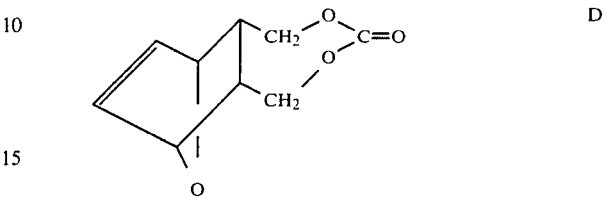

The cyclic carbonate D is then subjected to alcoholysis by reacting D with an alkanol (alkyl-OH) having from 1 to 12 carbons, such as ethanol, n-propanol, isopropanol, butanol, pentanol, hexanol, heptanol, octanol, nonenol or decanol, including all the various isomers thereof, preferably isopropyl alcohol, employing a molar ratio of D: alkanol of within the range of from about 1:10 to about 1:100 to form hydroxycarbonate E (which itself is a novel compound)

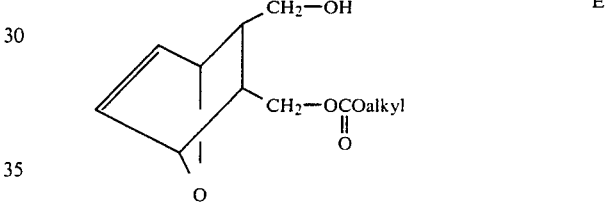

(wherein alkyl contains 1 to 12 carbons as defined herein).

Thereafter, the hydroxy carbonate E is tosylated (or otherwise protected) by reacting E (dissolved in methylene chloride, and a basic solvent such as pyridine, triethylamine or dimethylaminopyridine) with tosyl chloride or other protecting agent, such as methane sulfonyl chloride (mesyl chloride) and trifluoromethanesulfonic anhydride, to form the tosylate F or other protected compound

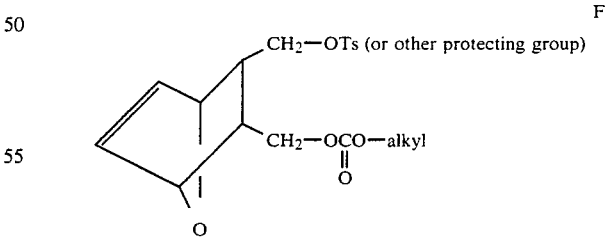

Then, the tosylate F dissolved in an inert solvent such as dimethylsulfoxide, or dimethylformamide is cyanated by reacting F with an alkali metal cyanide such as NaCN or KCN employing a molar ratio of IV:cyanide of within the range of from about 1:1 to about 10:1, at elevated temperatures of from about 80° C. to about 130° C., in an inert atmosphere, such as an argon atmosphere, to form the cyanocarbonate G (which itself is a new compound)

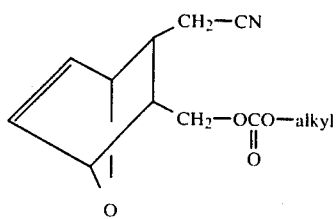

G

Cyanocarbonate G is dissolved in an alcohol such as methanol or ethanol and treated with aqueous alkali metal carbonate such as potassium carbonate at reduced temperature to form cyano-alcohol H

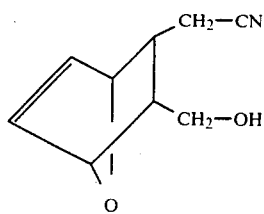

H which is made to undergo tetrahydropyranyl ether formation by reacting cyano alcohol H with dihydropyran in the presence of an inert organic solvent such as methylene chloride or ether and catalytic amount of p-toluene sulfonic acid at reduced temperatures of from about 0° C. to about 10° C., to form the tetrahydropyranyl ether of formula J

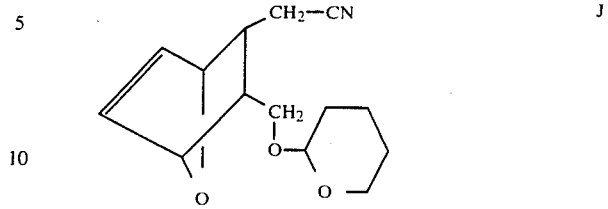

J

Compound J is then made to undergo epoxide formation by treating a solution of J in methylene chloride or other appropriate solvent with m-chloroperoxybenzoic acid at reduced temperatures to form epoxy nitrile II (which itself is a novel compound)

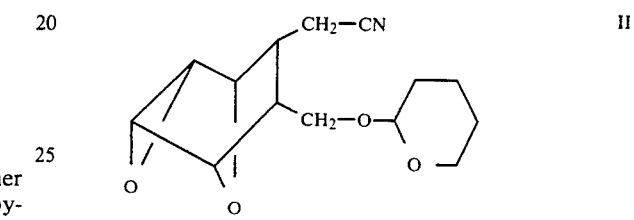

II (which is a novel compound).

The compounds of formula I of the invention may be formed starting with compound II in accordance with the followihg reaction sequence.

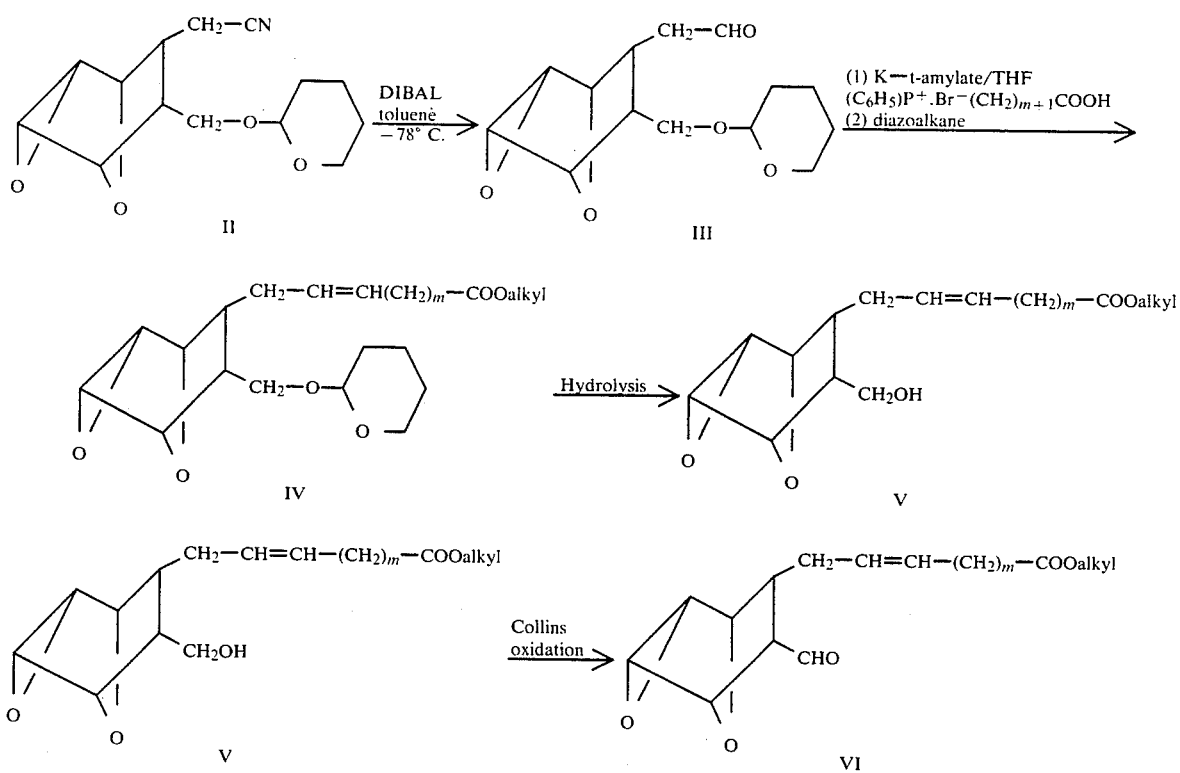

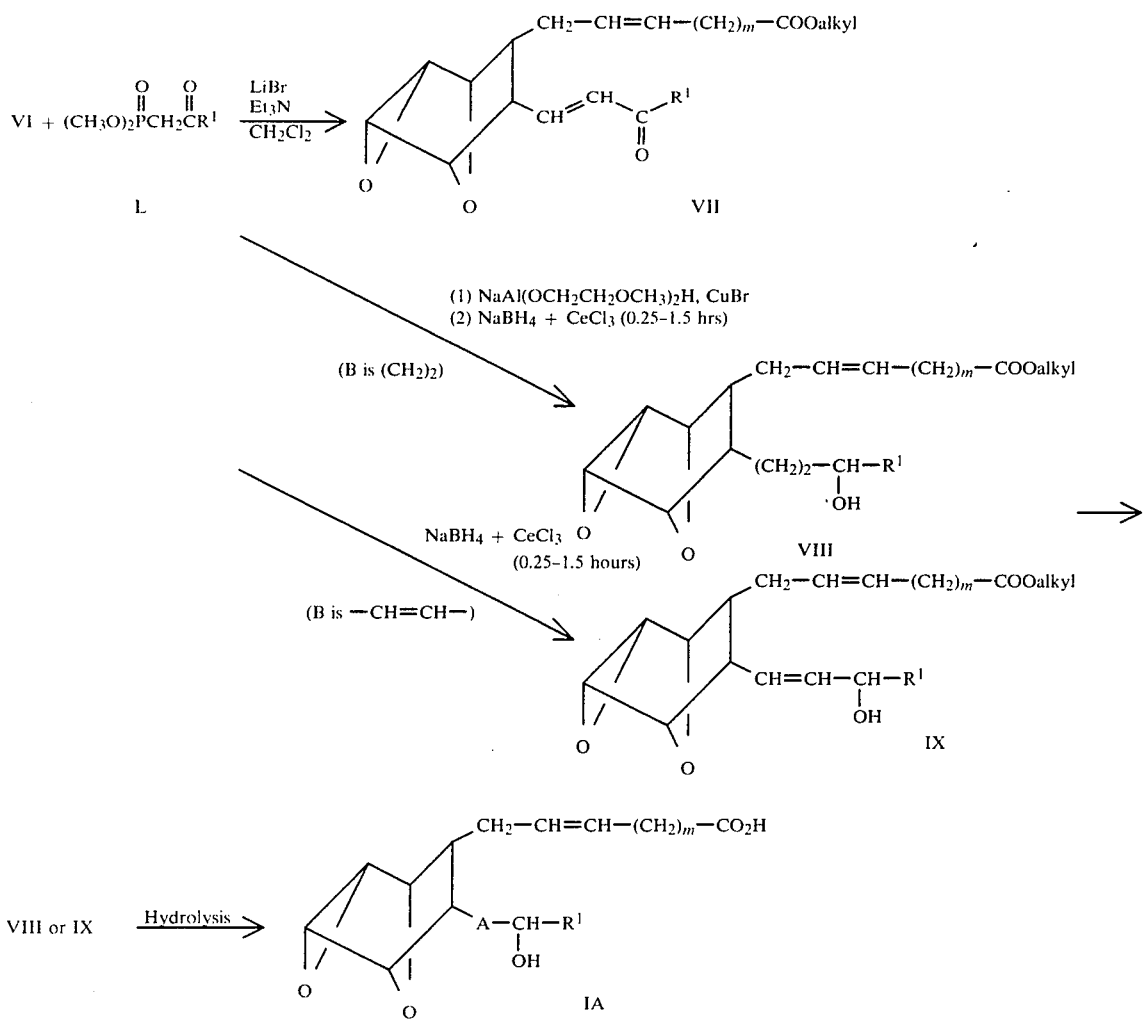

As seen from the reaction sequence set out above, compounds of the invention may be formed by treating II with diisobutyl aluminum hydride (DIBAL) in the presence of an inert solvent such as toluene or tetrahydrofuran at reduced temperatures of from about $-70°$ to about $-85°$ C. to form epoxy aldehyde III (which itself is a new compound)

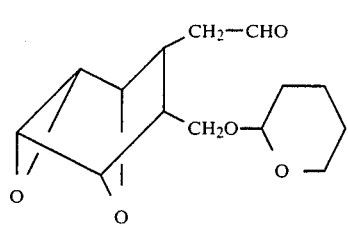

Epoxy aldehyde III in appropriate solvent such as tetrahydrofuran is then reacted with a suspension formed by mixing dry carboxyalkyltriphenylphosphonium halide K

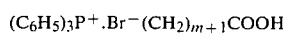

in tetrahydrofuran with potassium t-amylate in toluene at reduced temperature and the reaction product treated with ethereal diazoalkane to form the ester IV (which also is a novel compound)

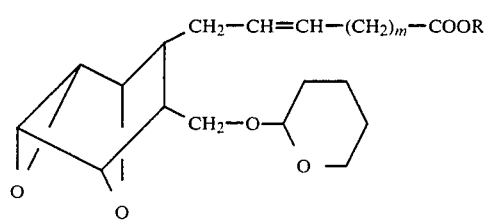

(wherein R is lower alkyl).

Compound IV is dissolved in methanol and is then hydrolyzed by treatment with strong acid such as HCl, Amberlyst resin or acetic acid to form alcohol V (which also is a novel compound)

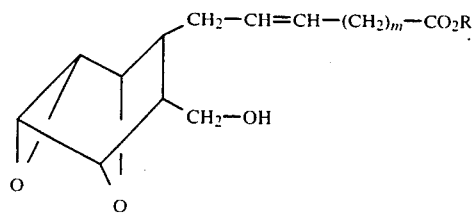

V (wherein R is lower alkyl).
which also is a novel compound.

The epoxy ester V containing the hydroxymethyl group is used to form epoxy aldehyde VI by subjecting epoxy ester V to Collins oxidation, for example, by reacting V with chromium oxide in pyridine. Aldehyde VI of the structure

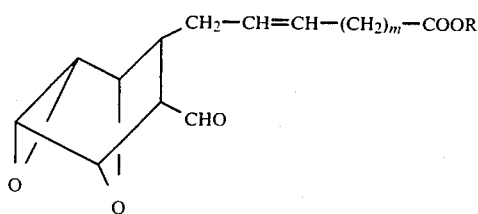

VI wherein R is lower alkyl (which also is a novel compound) is reacted with a dialkoxy phosphonate, such as of the structure

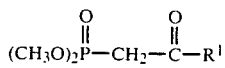

L employing a molar ratio of V:L of within the range of from about 1:1 to about 0.5:1, under basic conditions, such as triethylamine, diazabicyclo undecene (DBu) in the presence of anhydrous lithium bromide and an inert organic solvent, such as methylene chloride or acetonitrile to form epoxy compound VII of the structure

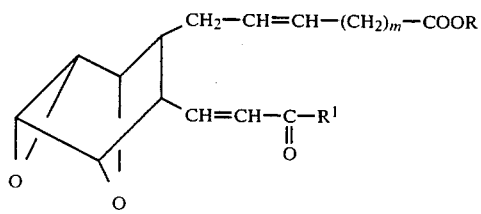

VII (wherein R is lower alkyl).
which also is a novel compound.

Compound VII may then be reduced by two different ways as outlined above to form compounds of the invention VIII or IX

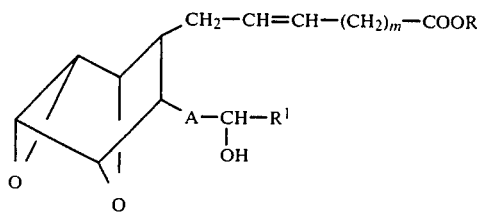

(wherein R is lower alkyl).
VIII—A is $(CH_2)_2$
IX—A is $-CH=CH-$
or compounds of the invention of the general formula X

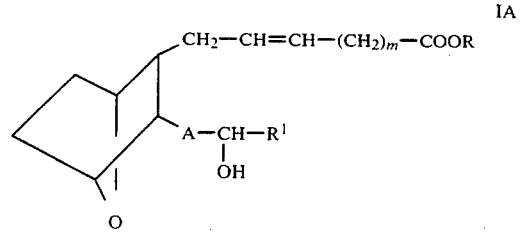

X (wherein R is lower alkyl).
Compounds of formula I

IA (wherein R is hydrogen).
may be prepared by hydrolyzing ester VIII or IX by treatment with a strong base such as sodium hydroxide or lithium hydroxide in the presence of an inert solvent such as tetrahydrofuran, methanol or dimethoxyethane-water to form the corresponding alkali metal salt which is then treated with strong acid such as HCl to form the acid compound of the invention IF.

The compounds of this invention have seven centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

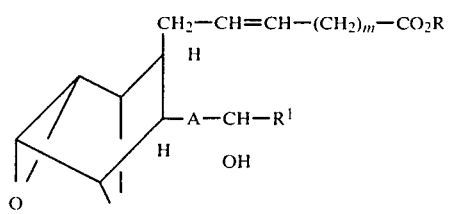

(cis-endo)

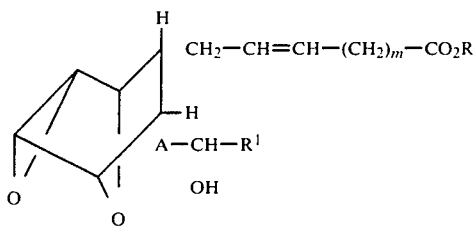

(cis-exo)

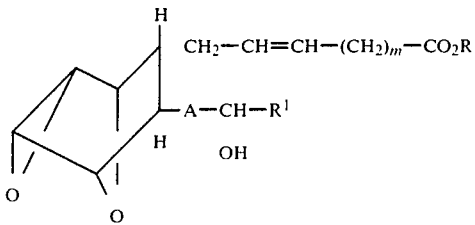

(trans)

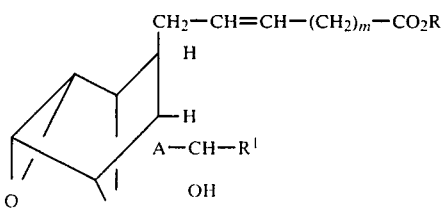

(trans)

The wavy line ( ) in the above formulae indicates that the hydroxy group in each of the compounds of formulae Ia–Id is either R($\beta$) or S($\alpha$).

The nucleus in each of the compounds of the invention is depicted as

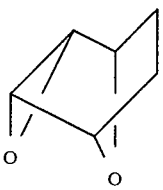

matter of convenience; it will also be appreciated that the nucleus in the compounds of the invention may be depicted as

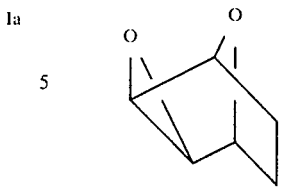

The compounds of this invention are cardiovascular agents useful as platelet aggregation inhibitors, such as inhibiting arachidonic acid-induced platelet aggregation (e.g., for treatment of thrombotic disease, such as coronary or cerebral thromboses) and in inhibiting broncho-constriction as induced by asthma. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1$\alpha$, 2$\beta$(5Z),3$\beta$(1E,3S),4$\alpha$5$\alpha$,6$\alpha$]-7-[5,6-Epoxy-3-(3-hydroxy-1-octenyl)-7-oxabicyclo[2.2.1]hept-2-yl]-5-heptenoic acid, methyl ester A. 7-Oxabicyclo[2.2.1]-5-hepten-2,3-dimethanol To a suspension of 6.84 g of lithium a hydride (180 mmol) in 200 ml of freshly distilled THF, cooled in an ice-water bath was added dropwise, a solution of 20 g of 7-oxabicyclo[2.2.1]-5-heptene-2,3-dicarboxylic anhydride (120 mmol) in 150 ml of dry THF, over a period of 1 hour. After the addition, the cooling bath was removed and the reaction mixture was stirred at room temperature for 24 hours. The reaction mixture was now cooled in an ice-water bath and excess of hydride was destroyed by slow addition of freshly prepared saturated sodium sulfate solution. Addition was continued until all the inorganic salts were precipitated as white granular solids. Anhydrous magnesium sulfate was added to the reaction mixture and it was filtered. The residue was thoroughly washed with methylene chloride. The residue was taken up in 500 ml of 10% acetonitrile in ethyl acetate, stirred for 30 minutes and finally was filtered. The combined filtrate was concentrated under reduced pressure. The crude residue was chromatographed on a silica gel column. Elution with 50% ethyl acetate in hexane followed by ethyl acetate and finally with 10% methanol in ethyl acetate afforded 17.25 g of title diol as a colorless viscous oil.

B. 7-Oxabicyclo[2 2.1]-5-heptene-2,3-dimethanol carbonate

To a solution of 16.73 g of Part A diol (107.4 mmole) in 200 ml of freshly distilled THF, cooled in an ice-water bath was added dropwise 90 ml of a 12.5% by weight solution of phosgene in toluene (112.5 mmol), over a period of 45 minutes. The reaction mixture was stirred for an additional 15 minutes, whereupon argon was bubbled through to remove excess of phosgene and hydrogen chloride formed during the reaction. The reaction mixture was now concentrated under reduced pressure. The crude monochloroformate was now dissolved in 250 ml of methylene chloride and cooled at $-50°$ C. in a dry ice-acetone bath. A solution of 25 ml of pyridine in 50 ml of methylene chloride was now added dropwise over a period of 20 minutes. An immediate white precipitate was formed upon addition. The reation mixture was left at $-50°$ C. for an additional 30 minutes, whereupon the cooling bath was removed and the reaction mixture was washed thoroughly with water. The methylene chloride layer was dried over anhydrous magnesium sulfate, filtered and the filtrate was concentrated under reduced pressure. The crude residue was triturated with ether, cooled at 0° C. and the precipitated title carbonate was filtered off. 15.25 g of white crystalline title carbonate was obtained.

C. 2-Hydroxymethyl-3-isopropyloxycarbonyl-oxymethyl-7-oxabicyclo[2.2.1]heptene To a suspension of 15.25 g of Part B cyclic carbonate (83.8 mmole) in 200 ml of isopropyl alcohol was added with stirring 1 g of p-toluene sulfonic acid. The reaction mixture was heated under reflux for 8 hours whereupon it was cooled and isopropanol was removed by distillation under reduced pressure. The crude residue was dissolved in methylene chloride and washed with aqueous sodium bicarbonate solution. The aqueous layer was extracted several times with methylene chloride. The combined methylene chloride extract was dried over anhydrous magnesium sulfate and was then concentrated under reduced pressure to obtain 22.53 g of title isopropyloxycarbonate as a viscous oil.

D. 2-p-Toluenesulfonyloxymethyl-3-isopro-pyloxycarbonyloxymethyl-7-oxabicyclo-2.2.1]heptene To a solution of 22.53 g of Part C isopropyloxycarbonate (84 mmole) in 100 ml of pyridine was added with stirring 19.2 g of p-toluene sulfonyl chloride (101 mmole) at 0°–5° C. The reaction mixture was stirred at room temperature for 24 hours, whereupon it was diluted with methylene chloride and washed thoroughly with water, saturated copper sulfate solution and finally with water. The combined aqueous layer was extracted with two 200 ml portions of methylene chloride. The combined methylene chloride extract was dried over anhydrous magnesium sulfate and finally was concentrated under reduced pressure. The crude residue was triturated with ether, cooled at 0° C. and the precipitate title tosylate (28.3 g) was filtered off. The mother liquor was concentrated and chromatographed on a silica gel column to obtain additional 5.2 g of crystalline title tosylate (eluting solvent 15–30% ethyl acetate in hexane).

E. 2-Cyanomethyl-3-isopropyloxycarbonyl-oxymethyl-7-oxabicyclo[2.2.1]heptene To a solution of 5.3 g of Part D tosylate (12.99 mmole) in 50 ml of dry dimethylsulfoxide was added with stirring 1.28 g of powdered sodium cyanide (26 mmole). The reaction mixture was placed on an oil bath (bath temperature 90°–95° C.) and heated for 2 hours. It was now cooled and diluted with 200 ml of ether. The reaction mixture was now thoroughly washed with water. The combined aqueous extract was extracted with two 150 ml of ether. The ether layer was now dried over anhydrous magnesium sulfate and concentrated under reduced pressure. The crude residue was chromatographed on a silica gel column. Elution with 25–50% ehtyl acetate in hexane afforded 2.58 g of title cyano-carbonate.

F. 2-Cyanomethyl-3-hyroxymethyl-7-oxabi-cyclo[2.2.1]heptene

To a solution of 1 g of potassium carbonate in 25 ml of water and 75 ml of methanol, cooled in an ice-water bath was added with stirring a solution of 2.58 g of Part E cyano-carbonate (9.8 mmol) in 10 ml of methanol. After 15 minutes, the cooling bath was removed and the reaction mixture was allowed to stand at room temperature for additional 6 hours, whereupon it was acidified with 1N aqueous hydrochloric acid solution. Most of methanol was now removed by distillation under reduced pressure. The residue was now exhaustively extracted with methylene chloride (X12) (after saturating it with sodium chloride). The combined organic extract was dried over anhydrous magnesium sulfate and concentrated under reduced pressure. The crude residue was chromatographed on a silica gel column and eluted with 25–50% ethyl acetate in hexane, followed by ethyl acetate to obtain 1.23 g of title cyano alcohol.

G. 2-Cyanomethyl-3-tetrahydropyranyloxy-methyl-7-oxabicyclo[2.2.1]heptene

A solution of 1.23 g of Part F cyano-alcohol (7.36 mmole) in 20 ml of dry methylene chloride was treated with 800 ml of dihydropyran (8.89 mmole) and catalytic amount of p-toluene sulfonic acid at 0°–5° C. After 4 hours, the reaction mixture was diluted with ether and washed with aqueous sodium bicarbonate solution. The aqueous layer was reextracted twice with ether. The combined organic extract was dried over anhydrous magnesium sulfate and concentrated under reduced pressure. The crude residue was chromatographed on a silica gel column and eluted with 2 ethyl acetate in hexane to obtain 1.61 g of title tetrahydropyranyl ether.

H. 5,6-Epoxy-2-cyanomethyl-3-tetrahydro-pyranyloxymethyl-7-oxabicyclo[2.2.1]-heptene A solution of 1.61 g of Part G cyano ether (6.4 mmole) in 20 ml of dry methylene chloride was treated with 1.66 g of 80% pure m-chloroperoxybenzoic acid (9.6 mmole) at 0°–5° C. After a few minutes, the cooling-bath was removed and the reaction mixture was let stand at room temperature for 6 hours. The reaction mixture was now diluted with ether and excess of peracid was decomposed by addition of aqueous sodium meta-bisulfite solution. After stirring for 30 minutes, the organic layer was separated and the aqueous layer was extracted twice with methylene chloride. The combined organic extract was dried over anhydrous magnesium sulfate and concentrated under reduced pressure. Purification by chromatography on a silica gel column (eluting solvent 25–67% ethyl acetate in hexane) afforded 1.57 g of title epoxide.

J.
5,6-Epoxy-2-formylmethyl-3-tetrahydro-pyranyloxymethyl-7-oxabicyclo[2.2.1]-heptene To a solution of Part H epoxy-nitrile (1.57 g, 5.88 mmole) in 25 ml of toluene, cooled at −78° C. in a dry ice-acetone bath was added with stirring, 6.8 ml of a 25% by weight solution of diisobutylaluminum hydride in toluene (∼12 mmole), dropwise over a period of 5 minutes. After 4 hours at −78° C., excess of hydride was destroyed by dropwise addition of 1 ml of glacial acetic acid. The cooling bath was removed and 20 g of silica gel was added to the reaction mixture with stirring, followed by 1.5 ml of water dropwise. Stirring was continued for 30 minutes, whereupon the reaction mixture was filtered and the residual silica gel was washed successively with THF, 5% acetonitrile in ethyl acetate and finally with acetone. The combined filtrate was concentrated under reduced pressure and the crude residue was chromatographed on a silica gel column. Elution with 50% ethyl acetate in hexane, followed by ethyl acetate afforded 1.16 g of title epoxyaldehyde which crystallized on standing at −20° C.

K.
[1α,2β(5Z),3β,4α,5α,6α]-7-[5,6-Epoxy-3-(tetrahydropyranyloxymethyl)-7-oxabicyclo[2.2.1]hept-2-yl]-5-heptenoic acid, methyl ester A suspension of 5.77 g of freshly dried carboxybutyltriphenylphosphonium bromide (13.03 mmol), in 50 ml of freshly distilled THF, cooled in an ice-water bath was treated dropwise with 12 ml of a 1.5 M solution of K-t-amylate in toluene (19.2 mmole). The yellow-orange suspension was stirred at 0° C. for 30 minutes and finally at room temperature 1 hour, whereupon it was cooled to −20° C. and a solution of 2.33 g of Part J epoxy aldehyde (8.69 mmole) in 10 ml of dry THF was added dropwise over a period of several minutes. An instant discolorization of the ylide solution was observed. The reaction mixture was stirred at −20° C. for 2 hours, whereupon it was warmed to 0° C. and left for 15 minutes, prior to addition of glacial acetic acid. The reaction mixture was now diluted with ether and washed with water. The ether extract was washed several times with saturated sodium bicarbonate solution. The combined aqueous extract was now washed with ether (X2). The aqueous layer was now carefully acidified with 1N aqueous hydrochloric acid to pH 2. It was now extracted with ether and then with methylene chloride. The combined ether and methylene chloride extract was dried over anhydrous magnesium sulfate and concentated under reduced pressure. The crude residue was diluted with 75 ml of ether, cooled in an ice-water bath and an etheral diazomethane solution was added dropwise until the color persisted. After 30 minutes, excess diazomethane was removed by bubbling argon through the reaction mixture. It was now concentrated and the crude residue was chromatographed on a silica gel column. Elution with 15–40% ethyl acetate in hexane afforded 1.27 g of title 5Z-ester (contaminated with 10–15% of undesired 5E ester).

L.
[1α,2β(5Z),3β,4α,5α,6α]-7-[5,6-Epoxy-3-hydroxymethyl-7-oxabicyclo[2.2.1]hept2-yl]-5-heptenoic acid, methyl ester To a solution of 1.27 g of Part K tetrahydropyranyl ether (3.46 mmole) in 30 ml of methanol was added with stirring 250 mg of powdered and dried Amberlyst-15. After 6 hours at room temperature, the reaction mixture was diluted with ether and anhydrous magnesium sulfate was added. It was now filtered and the residual solid was washed thoroughly with ether. The combined organic extract was dried over anhydrous magnesium sulfate and concentrated under reduced pressure. The crude residue was chromatographed on a silica gel column and eluted with 50–75% ethyl acetate in hexane to obtain 892 mg of alcohol ester.

M.
[1α,2β(5Z),3β,4α,5α,6α]-7-[5,6-Epoxy-3-formyl-7-oxabicyclo[2.2.1]hept-2-yl]-5-heptenoic acid, methyl ester To a suspension of 325 mg of pyridinium chlorochromate and 325 mg of celite in 20 ml of dry methylene chloride was added with stirring a solution of 211 mg Part L alcohol ester (0.75 mmole) in 2 ml of methylene chloride. After 4 hours at room temperature, the reaction mixture was diluted with 100 ml of ether and filtered through a pad of florisil. Florisil was washed several times with ether and ethyl acetate. The combined organic extract was washed with water, dried over anhydrous magnesium sulfate and was then concentrated under reduced pressure to obtain 174 mg of title aldehyde.

N.
[1α,2β(5Z),3β(1E),4α,5α,6α]-7-[5,6-Epoxy-3-(3-oxo-1-octenyl)-7-oxabicyclo[2.2.1]hept-2-yl]-5-heptenoic acid, methyl ester To a suspension of 90 mg of dry lithium bromide in 5 ml of dry methylene chloride was added with stirring 140 µl of triethylamine, followed by a solution of 222 mg dimethyl-(2-oxoheptyl) phosphonate (1 mmole) in 1 ml of methylene chloride. After stirring for 15 minutes at room temperature, a solution of 174 mg Part M aldehyde (0.62 mmole) in 3 ml of methylene chloride was added dropwise. The reaction was stirred overnight, whereupon it was diluted with ether and washed with water. The aqueous layer was extracted with ether (X2). The combined ether extract was dried over anhydrous magnesium sulfate and concentrated under reduced pressure. The crude oily residue was chromatographed on a silica gel column and eluted with 15–30% ethyl acetate in hexane to obtain 175 mg of title enone.

O.
[1α,2β(5Z),3β(1E,3S),4α,5α,6α]-7-[5,6-Epoxy-3-(3-hydroxy-1-octenyl)-7-oxabicyclo[2.2.1]hept-2-yl]-5-heptenoic acid, methyl ester (fast moving isomer)

and

P.

[1α,2β(5Z),3β(1E,3R),4α,5α,6α]-7-[5,6-Epoxy-3-(3-hydroxy-1-octenyl)-7-oxabicyclo[2.2.1]hept-2-yl]-5-heptenoic acid, methyl ester (slow moving isomer)

To a solution of 170 mg of Part N enone (0.45 mmole) in 5 ml of methanol and THF each, was added with stirring 170 mg of ceric chloride hydrate. After 10 minutes at room temperature, the homogeneous solution was cooled to −50° C. in a dry ice-acetone bath and 20 mg of solid sodium borohydride (0.5 mmole) was added. The reaction mixture was stirred at −50° C. for 1 hour, whereupon it was treated with aqueou ammonium chloride solution. The cooling bath was removed and the reaction mixture was diluted with ether. The organic layer was separated and the aqueous layer was reextracted successively with ether and methylene chloride. The combined organic extract was dried over anhydrous magnesium sulfate and concentrated. Purification by chromatography on a silica gel column and elution with 30-50% ethyl acetate in hexane afforded 130 mg of fast-moving alcohol epimer and 40 mg of slow-moving isomer.

EXAMPLE 2

[1α,2β(5Z),3β(1E,3S),4α,5α,6α]-7-[5,6-Epoxy-3-(3-hydroxy-1-octenyl)-7-oxabicyclo[2.2.1]hept-2-yl]-5-heptenoic acid (fast moving ester)

A solution of 130 mg of Example 1 fast-moving alcohol epimer (0.35 mmole) in 5 ml of distilled THF was treated with 2 ml of a 1N aqueous lithium hydroxide solution. After 8 hours at room temperature, the reaction mixture was diluted with ether and acidified to pH 1 by addition of 1N aqueous hydrochloric acid solution. The ether layer was separated and the aqueous layer was extracted with methylene chloride (X2). The combined organic extract was dried over anhydrous magnesium sulfate and concentrated under reduced pressure to obtain 120 mg of crude acid (contaminated with 10-15% of presumably 5E-isomer). Chromatography on a silica gel column and elution with 2-3% methanol in methylene chloride afforded 80 mg of pure title acid. Anal calcd for $C_{21}H_{32}O_5$: C, 69.20; H, 8.85. Found: C, 69.24; H, 8.84.

EXAMPLE 3

[1α,2β(5Z),3β(1E,3R),4α,5α,6α]-7-[5,6-Epoxy-3-(3-hydroxy-1-octenyl)-7-oxabicyclo[2.2.1]hept-2-yl]-5-heptenoic acid (slow moving isomer)

To a solution of 40 mg [1α,2β(5Z),3β(1E,3S),4α,5α,6α]-7-[5,6-epoxy-3-(3-hydroxy-octenyl)-7-oxabicyclo[2.2.1]hept-2-yl]-5-heptenoic acid, methyl ester slow-moving alcohol epimer (prepared as described in Example 1 Part P) (0.11 mmole) in 3 ml of distilled THF was added with stirring 1 ml of a 1N aqueous lithium hydroxide solution. After 8 hours at room temperature, the reaction mixture was diluted with ether and acidified with 1N aqueous hydrochloric acid solution of pH 1. The organic layer was separated and the aqueous layer was extracted with methylene chloride. The combined organic extract was dried with anhydrous magnesium sulfate and then concentrated under reduced pressure to obtain 33 mg of title acid as an oil.

Anal Calcd for $C_{21}H_{32}O_5$, 0.96 mole of $H_2O$: C, 66.06; H, 8.95. Found: C, 66.06; H, 8.47.

EXAMPLE 4

[1α,2β(5Z),3β(1E,3S),4α,5α,6α]-7-[5,6-Epoxy-3-(3-cyclohexyl-3-hydroxy-1-propenyl)-7-oxabicyclo[2.2.1]hept-2-yl]-5-heptenoic acid (fast moving isomer)

A.

[1α,2β(5Z),3β(1E),4α,5α,6α]-7-[5,6-Epoxy-3-(3-oxo-3-cyclohexyl-1-propenyl)-7-oxabicyclo[2.2.1]hept-2-yl]-5-heptenoic acid, methyl ester To a suspension of 135 mg of dry lithium bromide in 5 ml of methylene chloride was added with stirring 200 μl of triethylamine, followed by a solution of 350 mg 2-oxo-cyclohexyl(dimethyl)phosphonate (1.5 mmole) in 2 ml of methylene chloride. After stirring for 15 minutes at room temperature, a solution of 220 mg of [1α,2β(5Z),3β(1E,3S),4α,5α,6α]-7-[5,6-epoxy-3-formyl-7-oxybicyclo[2.2.1]hept-2-yl]-5-heptenoic acid, methyl ester prepared as described in Example 1 Part M in 3 ml of methylene chloride was added dropwise. The reaction mixture was stirred at room temperature for 3 hours whereupon it was diluted with ether and washed with water. The aqueous layer was extracted with ether (X2). The combined ether extract was dried over anhydrous magnesium sulfate and was then concentrated under reduced pressure. Chromatographic purification on a silica gel column (eluting solvent 10-30% ethyl acetate in hexane) gave 235 mg of desired title enone.

B.

[1α,2β(5Z),3β(1E,3S),4α,5α,6α]-7-[5,6-Epoxy-3-(3-cyclohexyl-3-hydroxy-1-propenyl)-7-oxabicyclo[2.2.1]hept-2-yl]-5-heptenoic acid, methyl ester (fast moving isomer)

and

C.

[1α,2β(5Z),3β(1E,3R),4α,5α,6α]-7-[5,6-Epoxy-3-(3-cyclohexyl-3-hydroxy-1-propenyl)-7-oxabicyclo[2,2,1]hept-2-yl]-5-heptenoic acid, methyl ester (slow moving isomer)

To a solution of 235 mg of Part A enone (0.61 mmole) in 5 ml of methanol and THF was added with stirring 235 mg ceric (111) chloride hydrate. After stirring for 10 minutes at room temperature, the reaction mixture was cooled to −50° C. and 25 mg of solid sodium borohydride (0.66 mmole) was added. After 1 hour at −50° C., the reaction mixture was quenched by addition of aqueous ammonium chloride solution. It was now warmed to room temperature and diluted with ether. The organic layer was separated and the aqueous layer was extracted with methylene chloride. The combined organic extract was dried over anhydrous magnesium sulfate and concentrated under reduced pressure. The crude residue was chromatographed on a silica gel column and eluted with 30-67% ethyl acetate in hexane to obtain 175 mg of B title fast-moving alcohol epimer and 35 mg of title C slow-moving alcohol epimer.

EXAMPLE 5

[1α,5β(5Z),3β(1E,3S),4α,5α,6α]-7-[5,6-Epoxy-3-(3-cyclohexyl-3-hydroxy-1-propenyl)-7-oxabicyclo[2.2.1]hept-2-yl]-5-heptenoic acid (fast moving isomer)

A solution of 175 mg of Example 4, Part B, alcohol-ester (fast moving isomer) in 5 ml of dry THF was treated with 2 ml of 1N aqueous lithium hydroxide solution. The reaction mixture was stirred at room temperature for 8 hours, whereupon it was acidified with 1N aqueous hydrochloric acid solution. It was then diluted with ether and the organic layer was separated. The aqueous layer was extracted with methylene chloride twice. The combined organic extract was dried over anhydrous magnesium sulfate and was then concentrated under reduced pressure to obtain 163 mg of crude acid. Chromatography on a silica gel column and elution with 3-5% methanol in methylene chloride afforded 110 mg of title acid.

Anal Calcd for $C_{22}H_{32}O_5$: C, 70.18; H, 8.57. Found: C, 70.03; H, 8.59.

EXAMPLE 6

[1α,2β(5Z),3β(1E,3R),4α,5α,6α]-7-[5,6-Epoxy-3-(3-cyclohexyl-3-hydroxy-1-propenyl)-7-oxabicyclo[2.2.1]hept-2-yl]-5-heptenoic acid (slow moving isomer)

To a solution of 35 mg Example 4 Part C slow-moving alcohol epimer (0.09 mmole) in 3 ml of distilled THF was added with stirring 1 ml of a 1N aqueous lithium hydroxide solution. After 8 hours at room temperature, the reaction mixture was diluted with ether and acidified to pH 1 with 1N aqueous hydrochloric acid solution. The organic layer was separated and the aqueous layer was extracted with methylene chloride. The combined organic extract was dried over anhydrous magnesium sulfate and finally was concentrated under reduced pressure to obtain 28 mg of title acid.

Anal Calcd for $C_{22}H_{32}O_5$, 0.27 mole of water: C, 69.28; H, 8.60. Found: C, 69.28; H, 8.71.

EXAMPLE 7

[1α,2β(5Z),3β(1E,3R,4S),4α,5α,6α]-7-[5,6-Epoxy-3-(3-hydroxy-4-phenyl-1-pentenyl)-7-oxabicyclo[2.2.1]hept-2-yl]-5-heptenoic acid, methyl ester

A.

[1α,2β(5Z),3β(1E,3R,4S),4α,5α,6α]-7-[5,6-Epoxy-[3-(3-oxo-4-phenyl-1-pentenyl)-7-oxabicyclo[2.2.1]hept-2-yl]]-5-heptenoic acid, methyl ester To a suspension of 90 mg of anhydrous lithium bromide (1 mmole) in 5 ml of dry methylene chloride was added with stirring 140 μl triethylamine (1 mmole). 256 mg of (+) dimethyl(2-oxo-3-methyl-3-phenyl) propyl phosphonate was then added dropwise. After 15 minutes at room temperature, a solution of Example 1 Part M 5,6-exo epoxy aldehyde (170 mg, 0.62 mmole) in 3 ml of methylene chloride was added slowly. The reaction mixture was stirred at room temperature overnight, whereupon it was diluted with ether and washed with water. The organic layer was dried over anhydrous magnesium sulfate, filtered and concentrated under reduced pressure. The crude oily residue was chromatographed on a silica gel column and eluted with 15-30% ethyl acetate in hexane to obtain 177 mg of title enone.

B.

[1α,2β(5Z),3β(1E,3R,4S),4α,5α,6α]-7-[5,6-Epoxy-3-(3-hydroxy-4-phenyl-1-pentenyl)-7-oxabicyclo[2.2.1]hept-2-yl]-5-heptenoic acid, methyl ester To a solution of 177 mg of Part A enone in 5 ml of dry methanol and 5 ml of distilled THF was added with stirring 175 mg of ceric (III) chloride hydrate. After 10 minutes at room temperature, the homogeneous solution was cooled to −50° C. in dry ice-acetone bath and 20 mg of solid so borohydride was added with stirring. After 1 hour at −50° C. the reaction mixture was quenched by addition of aqueous ammonium chloride solution, warmed to room temperature and was then diluted with ether. The organic layer was separated and the aqueous layer was extracted twice with ether and twice with methylene chloride. The combined organic extract was dried over anhydrous magnesium sulfate and concentrated under reduced pressure. The crude residue was chromatographed on a silica gel column and eluted with 20-50% ethyl acetate in hexane to obtain 133 mg of alcohol-ester as an oil.

EXAMPLE 8

[1α,2β(5Z),3β(1E,3R,4S),4α,5α,6α]-7-[5,6-Epoxy-3-(3-hydroxy-4-phenyl-1-pentenyl)-7-oxabicyclo[2.2.1]hept-2-yl]-5-heptenoic acid A solution of 133 mg Example 7 alcohol-ester (0.32 mmole) in 5 ml of distilled THF was treated with 2 ml of 1N aqueous lithium hydroxide solution. The reaction mixture was stirred at room temperature for 16 hours, whereupon it was carefully acidified to pH 1 by addition of 1N aqueous hydrochloric acid solution. It was now diluted with ether and the organic layer was separated. The aqueous layer was extracted with methylene chloride (X2). The combined organic extract was dried over anhydrous magnesium sulfate and concentrated under reduced pressure to obtain 124 mg crude acid, contaminated with ~15% of α-side chain olefin isomer. Chromatograpny on a silica gel column and elution with 1-3% methanol in methylene chloride afforded 51 mg or title acid as an oil.

Anal Calcd for $C_{24}H_{30}O_5$: C, 72.33; H, 7.59. Found: C, 72.32; H, 7.57.

EXAMPLE 9

[1α,2β(5Z),3β(1E,3S),4α,5α,6α]-7-[5,6-Epoxy-3-(3-hydroxy-3-phenyl-1-propenyl)-7-oxabicyclo[2.2.1]hept-2-yl]-5-heptenoic acid Following the procedure of Examples 7 and 8 except substituting dimethyl(2-oxo-2-phenyl)ethyl phosphonate for (+)dimethyl(2-oxo-3-methyl-3-phenyl)propyl phosphonate, acid, the title compound is obtained.

EXAMPLE 10

[1α,2β(5Z),3β(1E,3S),4α,5α,6α]]-7-[5,6-Epoxy-3-(3-hydroxy-4-phenyl-1-butenyl)-7-oxabicyclo[2.2.1]hept-2-yl]-5-heptenoic acid Following the procedure of Examples 7 and 8 except substituting dimethyl(2-oxo-4-phenyl)butyl phosphonate for (+)dimethyl(2-oxo-3-methyl-3-phenyl)propyl phosphonate, the title compound is obtained.

EXAMPLE 11

[1α,2β(5Z),3β(1E,3S)4α,5α,6α]-7-[5,6-Epoxy-3-(3-hydroxy-5-phenyl-1-pentenyl)-7-oxabicyclo[2.2.1]hept-2-yl]-5-heptenoic acid, methyl ester

A.

[1α,2β(5Z),3β(1E),4α,5α,6α]-7-[5,6-Epoxy-3-(3-oxo-5-phenyl-1-pentenyl)-7-oxabicyclo[2.2.1]hept-2-yl]-5-heptenoic acid, methyl ester To a suspension of 135 mg anhydrous lithium bromide (1.56 mmole) in 3 ml of dry methylene chloride was added with stirring 198 μl triethylamine (1.42 mmole). 386 mg dimethyl(2-oxo-4-phenyl)butyl phosphonate (1.51 mmole) in 1 ml of methylene chloride was now added dropwise. After 30 minutes at room temperature, a solution of Example 1 Part M 5,6-exo-epoxy aldehyde (200 mg, 0.7 mmole) in 3 ml of methylene chloride was added dropwise. The reaction mixture was stirred at room temperature overnight, whereupon it was diluted with ether and washed with water. The organic layer was dried over anhydrous magneisum sulfate and concentrated under reduced pressure. The crude residue was chromatographed on a silica gel column and eluted with 40% ethyl acetate in hexane to obtain 208 mg of title enone.

B.
[1α,2β(5Z),3β(1E,3S),4α,5α,6α]-7-[5,6-Epoxy-3-(3-hydroxy-5-phenyl-1-pentenyl)-7-oxabicyclo[2.2.1]hept-2-yl]-5-heptenoic acid, methyl ester To a solution of 208 mg of Part A enone (0.5 mmole) in 1 ml of methanol and 1 ml of methylene chloride was added with stirring 124 mg ceric chloride hydrate. After 10 minutes at room temperature, the homogeneous solution was cooled to −50° C. and 19 mg of solid sodium borohydride (0.5 mmole) was added. The reaction mixture was let stand at −50°C. for 3 hours, whereupon it was treated with aqueous ammonium chloride solution. The cooling bath was removed and the reaction mixture was diluted with ether. The organic layer was separated and the aqueous layer was extracted successively with ether and methylene chloride. The combined organic extract was dried over anhydrous magnesium sulfate and concentrated. The crude residue was chromatographed on a silica gel column and eluted with 40% ethyl acetate in hexane to obtain 114 mg of title fast moving alcohol epimer and 40 mg of slow moving isomer.

EXAMPLE 11A

[1α,2β(5Z),3β(1E,3S),4α,5α,6α]-7-[5,6-Epoxy-3-(3-hydroxy-5-phenyl-1-pentenyl)-7-oxabicyclo[2.2.1]hept-2-yl]-5-heptenoic acid A solution of 114 mg of Example 11 ester (0.27 mmole) in 1 ml of THF and 1 ml of 1N aqueous lithium hydroxide was stirred at 25° C. for 2 hours. The reaction mixture was concentrated and then acidified with oxalic acid solution to pH 3. It was now extracted with ether (X3). The combined ether extract was dried over anhydrous magnesium sulfate and concentrated under reduced pressure to give 100 mg crude oil. Purifications on preparative silica gel plates (eluting solvent 10% in methylene chloride) gave 37 mg of title acid.

Anal Calcd for $C_{24}H_{30}O_5$: C, 72.33; H, 7.59. Found: C, 72.10; H, 7.59.

EXAMPLE 12

[1α,2β(5Z),3β(1E,3S)4α,5α,6α]-7-[5,6-Epoxy-3-(3-hydroxy-4-cyclopentyl-1-butenyl)-7-oxabicyclo[2.2.1-]hept-2-yl]-5-heptenoic acid Following the procedure of Examples 7 and 8 except substituting dimethyl(2-oxo-3-cyclopentyl)propyl phosphonate for (+)dimethyl(2-oxo-3-methyl-3-phenyl)propyl phosphonate, the title compound is obtained.

EXAMPLE 13

[1α,2β(5Z),3β(1E,3S)4α,5α,6α]-7-[5,6-Epoxy-3-(3-hydroxy-1,5-hexadienyl)-7-oxabicyclo[2.2.1]hept-2-yl]-5-heptenoic acid Following the procedure of Examples 7 and 8 except substituting dimethyl(2-oxo-4-pentenyl)phosphonate for (+)dimethyl(2-oxo-3-methyl-3-phenyl)propyl phosphonate, the title compound is obtained.

EXAMPLE 14

[1α,2β(5Z),3β(1E,3S)4α,5α,6α]-7-[5,6-Epoxy-3-(3-hydroxy-1-nonenyl)-7-oxabicyclo[2.2.1]hept-2-yl]-5-heptenoic acid Following the procedure of Examples 7 and 8 except substituting dimethyl(2-oxo-octyl)phosphonate for (+)dimethyl(2-oxo-3-methyl-3phenyl)-propyl phosphonate, the title compound is obtained.

EXAMPLE 15

[1α,2β(5Z),3β(1E,3S)4α,5α,6α]-7-[5,6-Epoxy-3-(3-hydroxy-1-pentenyl)-7-oxabicyclo[2.2.1]hept-2-yl]-5-heptenoic acid Following the procedure of Examples 7 and 8 except substituting dimethyl(2-oxo-butyl)phosphonate for (+)dimethyl(2-oxo-3-methyl-3-phenyl)propyl phosphonate, the title compound is obtained.

EXAMPLE 16

[1α,2β(5Z),3β(3R,4S),4α,5α,6α]-7-[5,6-Epoxy-3-(3-hydroxy-4-phenyl-1-pentyl)-7-oxabicyclo[2.2.1]-hept-2-yl]-5-heptenoic acid A. [1α,2β(5Z),3β(3R,4S),4α,5α,6α]-7-[5,6-Epoxy-3-(3-hydroxy-4-phenyl-1-pentyl)-7-oxabicyclo[2.2.1-]hept-2-yl]-5-heptenoic acid, methyl ester To a suspension of 686 mg of purified cuprous bromide (4.8 mmole) in 12 ml of dry THF, cooled at 0°–5° C. is added with stirring 1.35 ml of a 3.5M solution of red-Al (sodium bis(2-methoxyethoxy)aluminum hydride) in toluene dropwise. The solution is stirred at 0°–5° C. for 30 minutes, whereupon it is cooled to −78° C. and 2ml of n-butanol (18 mmole) is added rapidly, followed by a solution of 672 mg of Example 7 Part A enone (2 mmole) in 4 ml of dry THF. After 10 minutes at −78° C., the reaction mixture is warmed to −20° C. and left for an additional 1 hour. The reaction mixture is quenched by addition of 70 ml of water and then poured into saturated ammonium chloride solution and extracted with ether (X3). The ether extract is dried over anhydrous magnesium sulfate, filtered and the filtrate is concentrated under reduced pressure. 675 Mg of desired title ketone is obtained.

To a solution of 338 mg of ketone (1 mmole) (prepared as described above) in 2 ml of methanol and 2 ml of dry THF is added with stirring 400 mg of ceric (III) chloride hydrate (1 mmole). After stirring at room temperature for 10 minutes, the reaction mixture is cooled to −50° C. and 38 mg of solid sodium borohydride (∼1 mmole) is added to the reaction mixture. The reaction mixture is stirred at −50° C. for 45 minutes, whereupon 5 ml of acetone is added to destroy excess of borohydride. The mixture is stirred for an additional 5 minutes at −50° C. The cooling bath is removed and the reaction mixture is evaporated to dryness. The crude residue is diluted with ether and washed with 1N aqueous hydrochloric acid solution. The ether extract is dried over anhydrous $MgSO_4$ and concentrated under reduced pressure. The crude residue is chromatographed on a silica gel column and eluted with ethyl acetate (30–50%) in hexane to obtain the desired title alcohol.

B.
[1α,2β(5Z),3β(3R,4S),4α,5α,6α]-7-[5,6-Epoxy-3-(3-hydroxy-4phenyl-1-pentyl)-7-oxabicyclo[2.2.1]hept-2-yl]-5-heptenoic acid Following the procedure of Example 8 except substituting the above Part A alcohol ester for the Example 7 alcohol ester, the title compound is obtained.

EXAMPLE 17

[1α,2β(5Z),3β(3S),4α,5α,6α]-7-[5,6-Epoxy-3-(3-hydroxy-3-phenyl-1-propyl)-7-oxabicyclo[2.2.1]hept-2-yl]heptenoic acid Following the procedure of Example 16 and Examples 7 and 8 except substituting benzoic acid for 2-phenylpropionic acid, the title compound is obtained.

EXAMPLE 18

[1α,2β(5Z),3β(3S),4α,5α,6α]-7-[5,6-Epoxy-3-(3-hydroxy-4-phenyl-1-butyl)-7-oxabicyclo[2.2.1]hept-2-yl]-5-heptenoic acid Following the procedure of Example 16 and Examples 7 and 8 except substituting phenylacetic acid for 2-phenylpropionic acid, the title compound is obtained.

EXAMPLE 19

[1α,2β(5Z),3β(3S),4α,5α,6α]-7-[5,6-Epoxy-3-(3-hydroxy-3-cyclohexyl-1-propyl)-7-oxabicyclo[2.2.1]hept-2-yl]-5-heptenoic acid Following the procedure of Example 16 and Examples 7 and 8 except substituting cyclohexylcarboxylic acid for 2-phenylpropionic acid, the title compound is obtained.

EXAMPLES 20 to 29

Following the procedure of Examples 7 and 8 (where A is CH=CH) and Example 16 (where A is (CH$_2$)$_2$), except substituting for carboxybutyltriphenylphosphonium bromide, the compound shown in Column I of Table I set out below and substituting for (+)dimethyl(2-oxo-3-methyl-3-phenyl)propyl phosphonate, the compound shown in Column II, the compound of the invention shown in Column III is obtained.

TABLE I

| | Column I | Column II | | | Column III |
| Ex. No. | $(C_6H_5)_3{}^+P.Br^-(CH_2)_{m+1}COOH$ m | $(CH_3O)_2-\overset{O}{\underset{\|}{P}}-CH_2-\overset{O}{\underset{\|}{C}}-R^1$ R¹ | A | m | R¹ |
|---|---|---|---|---|---|
| 20. | 2 | CH$_3$ | CH=CH | 2 | CH$_3$ |
| 21. | 3 | C$_6$H$_5$ | (CH$_2$)$_2$ | 3 | C$_6$H$_5$ |
| 22. | 3 | C$_6$H$_5$CH$_2$ | CH=CH | 3 | C$_6$H$_5$CH$_2$ |
| 23. | 4 |  | (CH$_2$)$_2$ | 4 |  |
| 24. | 4 | 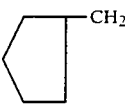 | CH=CH | 4 | 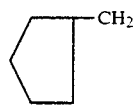 |
| 25. | 5 | CH$_3$—CH=CH— | (CH$_2$)$_2$ | 5 | CH$_3$—CH=CH— |
| 26. | 4 | C$_2$H$_5$ | CH=CH— | 1 | C$_2$H$_5$ |
| 27. | 4 | 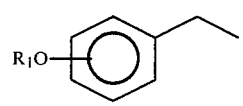 (R$_1$ = H or alkyl) | (CH$_2$)$_2$ | 1 |  (R$_1$ = H or alkyl) |
| 28. | 2 | | CH=CH | 2 | |
| 29. | 3 | CH$_3$CH$_2$—CH=CH— | (CH$_2$)$_2$ | 3 | CH$_3$CH$_2$—CH=CH— |

EXAMPLE 30

[1α,2β(5Z),3β(1E),4α,6α,5α]-7-[5,6-Epoxy-3-[3-hydroxy-3-(1-methylcyclohexyl)-1-propenyl]-7-oxabicyclo[2.2.1]hept-2-yl]-5-heptenoic acid, methyl ester

A.

[1α,2β(5Z),3β(1E),4α,5α,6α]-7-[5,6-Epoxy-3-[3-oxo-3-(1-methylcyclohexyl)-1-propenyl]-7-oxabicyclo[2.2.1]hept-2-yl]-5-heptenoic acid, methyl ester To a slurry of 135 mg of lithium bromide (1.56 mmole, 2.2 equiv.) in 3 ml of dry methylene chloride at 25° C. was added a solution of 293 mg of dimethyl [2-(1-methylcyclohexyl)]-2-oxo-ethyl phosphonate (1.5 mmole, 2.1 equiv.) in 1 ml of methylene chloride and 198 ml of triethylamine (1.42 mmole, 2.01 equiv.). After stirring for 30 minutes, a solution of ca. 0.70 mmole of [1α,2β-(5Z),3β(1E),4α,5α,6α]-7-[5,6-epoxy-3-formyl-7-oxabicyclo[2.2.1]hept-2-yl]-5-heptenoic acid, methyl ester (prepared as described in Example 1 Part M) in 1 ml of methylene chloride was added. The stirring was continued at 25° C. for 18 hours. The reaction mixture was then treated with 5 ml of 1M $NaH_2PO_4$ solution and diluted with 30 ml of ether. The layers were separated. The organic layer was washed with 10 ml of a saturated $KHCO_3$ solution, 10 ml of $H_2O$ and 10 ml of brine. The organic layer was then dried ($MgSO_4$) and concentrated.

The residue was purified on a silica gel column. Elution with 25% EtOAc/hexane gave 170 mg of title enone as a clear oil.

B.

[1α,2β(5Z),3β(1E,3S),4α,5α,6α]-7-[5,6-Epoxy-3-[3-hydroxy-3-(1-methylcyclohexyl)-1-propenyl]-7-oxabicyclo[2.2.1]hept-2-yl]-5-heptenoic acid, methyl ether To a solution of 170 mg of Part A enone (0.42 mmole) in 1 ml of methanol and 1 ml of THF at 25° C. was added 102.9 mg of cerium trichloride (0.42 mmole, 1 equiv.). After stirring at 25° C. for 15 minutes, the mixture was cooled to −50° C. and 15.9 mg of sodium borohydride 6.42 mmole, 4 equiv. was added. The mixture was stirred at −50° C. for 3 hours, then poured into 30 ml of a saturated solution of ammonium chloride. The aqueous solution was extracted with three 15 ml portions of ether. The combined extract was washed with 10 ml of $H_2O$, dried ($MgSO_4$) and concentrated. The residue was purified on a silica gel column. Elution with 25% of EtOAc/hexane gave 128 mg of title alcohol ester.

EXAMPLE 31

1α,2β(5Z),3β(1E,3S),4α,5α,6α]-7-[5,6-Epoxy-3-[3-hydroxy-3-(1-methylcyclohexyl)-1-propenyl]-7-oxabicyclo[2.2.1]hept-2-yl]-5-heptenoic acid A mixture of 128 mg of Example 30 alcohol ester (0.31 mmole), 1 ml of 1N LiOH (1.0 mmole, 3 equiv.) in 1 ml of THF was stirred at 25° C. for 2 hours and then concentrated. The residue was diluted with 5 ml of $H_2O$, acidifying to pH 3 with a saturated solution of oxalic acid, then extracted with three 15 ml portions of ether. The combined ethereal extract was washed with 15 ml of $H_2O$, dried ($MgSO_4$) and concentrated to give 112 mg of a crude oil.

This oil was purified on a silica gel preparative plate (50 mg batches, 0.5 mm silica gel plate, 10% MeOH/$CH_2Cl_2$) to yield a total of 49.6 mg of clean acid product.

TLC: silica gel; 10% MeOH/$CH_2Cl_2$; $R_f$~0.60.

Anal Calcd for $C_{23}H_{34}O_5.0.5\ H_2O$: C, 69.10; H, 8.82. Found: C, 69.10; H, 8.51.

EXAMPLE 32

[1α,2β(5Z),3β(1E,3S),4α,5α,6α]-7-[5,6-Epoxy-3-(3-hydroxy-4,4-dimethyl-1-octenyl)-7-oxabicyclo[2.2.1]hept-2-yl]-5-heptenoic acid, methyl ester

A.

[1α,2β(5Z),3β(1E),4α,5α,6α]-7-[5,6-Epoxy-3-(3-oxo-4,4-dimethyl-1-octenyl)-7-oxabicyclo[2.2.1]hept-2-yl]-5-heptenoic acid, methyl ester To a slurry of 102 mg of lithium bromide (1.17 mmol, 2.2 equiv.) in 3 ml of dry $CH_2Cl_2$ at 25° C. was added a solution of 293 mg of 3,3-dimethyl-2-oxo-heptyldimethylphosphonate (1.11 mmole, 2.1 equiv.) in 1 ml of $CH_2Cl_2$ and 148 ml of triethylamine (1.06 mmole, 2.01 equiv.). After stirring at 25° C. for 30 minutes, a solution of ca. 0.53 mmole of [1α,2β(5Z),3β(1E),4α,5α,6α]-7-[5,6-epoxy-3-formyl-7-oxabicyclo[2.2.1]hept-2-yl]-5-heptenoic acid, methyl ester (prepared as described in Example 1 Part M) in 1 ml of $CH_2Cl_2$ was added. The stirring was continued at 25° C. for 18 hours. The reaction mixture was then treated with 5 ml of 1M $NaH_2PO_4$ solution, and diluted with 30 ml of ether. The layers were separated. The organic layer was washed with 1 ml of a saturated $KHCO_3$ solution, 10 ml of $H_2O$ and 10 ml of brine. The organic layer was then dried ($MgSO_4$) and concentrated.

The residue was purified on a silica gel column. Elution with 25% EtOAc/hexane gave 130 mg of title enone as a clear oil.

B.

[1α,2β(5Z),3β(1E,3S),4α,5α,6α]-7-[5,6-Epoxy-3-(3-hydroxy-4,4-dimethyl-1-octenyl)-7-oxabicyclo[2.2.1]hept-2-yl]-5-heptenoic acid, methyl ester To a solution of 130 mg of Part A enone (0.32 mmole) in 1 ml of methanol and 1 ml of THF at 25° C. was added 78.4 mg of cerium trichloride 0.32 mmole, 1 equiv.). After stirring at 25° C. for 15 minutes, the mixture was cooled to −50° C. and 12.1 mg of sodium borohydride (0.32 mmole, 4 equiv.) was added. The mixture was stirred at −50° C. for 3 hours, then poured into 30 ml of a saturated solution of ammonium chloride. The aqueous solution was extracted with three 15 ml portions of ether. The combined extract was washed with 10 ml of $H_2O$, dried ($MgSO_4$) and concentrated. The residue was purified on a silica gel column. Elution with 25% EtOAc/hexane gave 96 mg of title alcohol ester.

EXAMPLE 33

[1α,2β(5Z),3β(1E,3S),4α,5α,6α]-7-[5,6-Epoxy-3-(3-hydroxy-4,4-dimethyl-1-octenyl)-7-oxabicyclo-[2.2.1]hept-2-yl]-5-heptenoic acid A mixture of 96 mg of Example 31 alcohol ester (0.23 mmole), 1 ml of 1N LiOH (1.0 mmole, 4 equiv.) in 1 ml of THF was stirred at 25° C. for 2 hours, then concentrated. The residue was diluted with 5 ml of $H_2O$, acidifying to pH 3 with a saturated solution of oxalic acid, then extracted with three 15 ml portions of ether. The combined ethereal extract was washed with 15 ml of $H_2O$, dried ($MgSO_4$) and concentrated to give 75 mg of a crude oil.

What is claimed is:

1. A compound having the structural formula

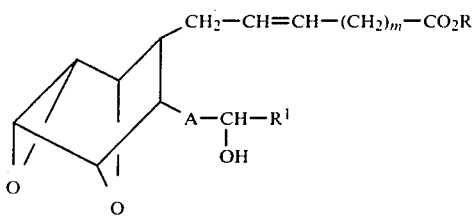

and including all stereoisomers thereof;

wherein m is 1 to 5; A is —CH=CH— or (CH$_2$)$_2$; R is H, lower alkyl, alkali metal or polyhydroxylamine; and R$^1$ is lower alkyl, aryl, aralkyl, cycloalkyl, cycloalkylalkyl or lower alkenyl containing 2 to 12 carbons, wherein lower alkyl or alkyl alone or as part of another group contains 1 to 12 carbons and is unsubstituted or is substituted with halo, hydroxy, amino, alkylamino, CF$_3$, alkoxy, aryl, alkyl-aryl, haloaryl, cycloalkyl, alkylcycloalkyl, nitro, cyano, thiol or alkylthio;

aryl alone or as part of another group contains 6 to 10 carbons in the ring portion and is unsubstituted or is substituted with 1 or 2 lower alkyl groups, 1 or 2 halogens, an aryl group, 1 or 2 hydroxy groups, 1 or 2 lower alkoxy groups, 1 or 2 alkylamino groups, 1 or 2 amino groups, 1 or 2 nitro groups, 1 or 2 cyano groups, 1 or 2 thiol groups, or 1 or 2 alkylthio groups;

cycloalkyl alone or as part of another group contains 3 to 12 carbons and is unsubstituted or is substituted with 1 or 2 halogens, 1 or 2 lower alkyl groups, and/or 1 or 2 lower alkoxy groups, an aryl group, 1 or 2 hydroxyl groups, 1 or 2 alkylamino groups, 1 or 2 amino groups, 1 or 2 nitro groups, 1 or 2 cyano groups, 1 or 2 thiol groups or 1 or 2 alkylthio groups; and (CH$_2$)$_m$ includes a straight or branched chain radical having 1 to 5 carbons in the normal chain and may contain 1 or 2 lower alkyl or halo substituents.

2. The compound as defined in claim 1 wherein m is 2 to 4.

3. The compound as defined in claim 1 wherein A is —CH=CH—.

4. The compound as defined in claim 4 wherein R$^1$ is butyl, pentyl, hexyl, heptyl, 1,1-dimethylpentyl, or 2-phenylethyl.

5. The compound as defined in claim 1 having the name [1α,2β(5Z),3β(1E,3S),4α,5α,6α]-7-[5,6-epoxy-3-(3-hydroxy-1-octenyl)-7-oxabicyclo[2.2.1]hept-2-yl]-5-heptenoic acid, or its methyl ester, including all stereoisomers thereof.

6. The compound as defined in claim 1 having the name [1α,2β(5Z),3β(1E,3S),4α,5α,6α]-7-[5,6-epoxy-3-(3-cyclohexyl-3-hydroxy-1-propenyl)-7-oxabicyclo[2.2.1]hept-2-yl]-5-heptenoic acid, including the methyl esters thereof, and including all stereoisomers thereof.

7. The compound as defined in claim 1 having the name [1α,2β(5Z),3β(1E,3R,4S),4α,5α,6α]-7-[5,6-epoxy-3-(3-hydroxy-4-phenyl-1-pentenyl)-7-oxabicyclo[2.2.1]hept-2-yl]-5-heptenoic acid, including the methyl ester thereof, and including all stereoisomers thereof.

8. The compound as defined in claim 1 having the name [1α,2β(5Z),3β(1E,3S),4α,5α,6α]-7-[5,6-epoxy-3-(3-hydroxy-5-phenyl-1-pentenyl)-7-oxabicyclo[2.2.1]hept-2-yl]-5-heptenoic acid including the methyl ester thereof, and including all stereoisomers thereof.

9. The compound as defined in claim 1 having the name [1α,2β(5Z),3β(1E,3S),4α,5α,6α]-7-[5,6-epoxy-3-(3-hydroxy-4,4-dimethyl-1-octenyl)-7-oxabicyclo[2.2.1]hept-2-yl]-5-heptenoic acid including the methyl ester thereof, and including all stereoisomers thereof.

10. The compound as defined in claim 1 having the name [1α,2β(5Z),3β(1E,3S),4α,5α,6α]-7-[5,6-epoxy-3-[3-hydroxy-3-(1-methylcyclohexyl)-1-propenyl]-7-oxabicyclo[2.2.1]hept-2-yl]-5-heptenoic acid including the methyl ester thereof, and including all stereoisomers thereof.

11. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier thereof.

14. A method of inhibiting bronchoconstriction associated with asthma or for treating peripheral vascular disease, which comprises administering to a mammalian host an effective amount of a compound as defined in claim 1 or a pharmaceutically acceptable salt thereof.

15. A compound having the structure

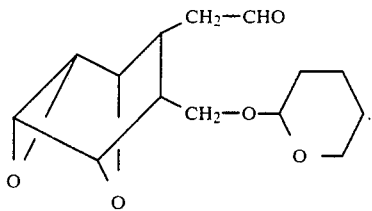

16. A compound having the structure

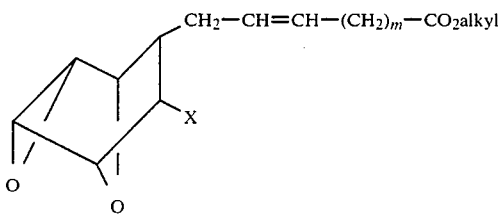

wherein X is

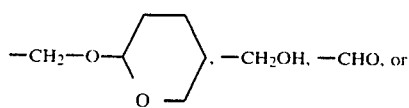, —CH$_2$OH, —CHO, or
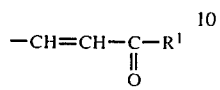
wherein m is 1–5, and R$^1$ *is lower alkyl, aryl, aralkyl, cycloalkyl, cycloalkylalkyl or lower alkenyl.*
17. The compound as defined in claim 16 having the structure
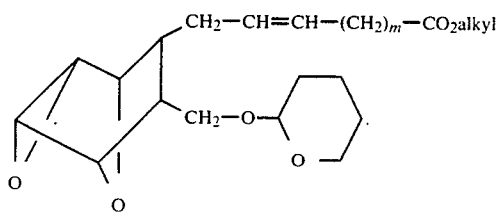
18. The compound as defined in claim 16 having the structure
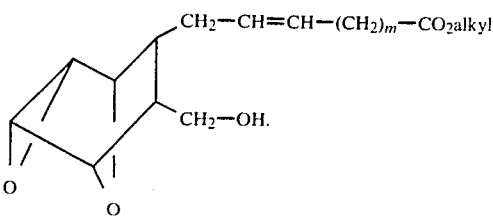
19. The compound as defined in claim 16 having the structure
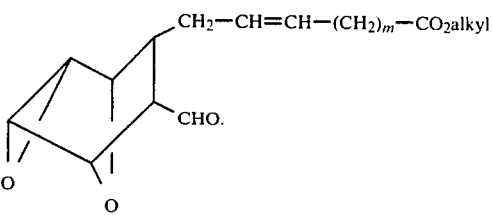
20. The compound as defined in claim 16 having the structure
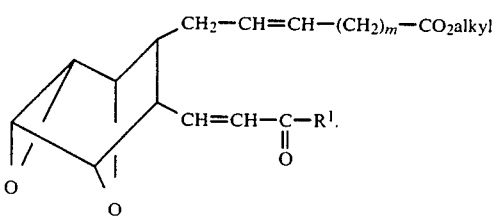
* * * * *

UNITED STATES PATENT AND TRADEMARK OFFICE
CERTIFICATE OF CORRECTION

PATENT NO. : 4,611,005
DATED : September 9, 1986
INVENTOR(S) : Jagabandhu Das

It is certified that error appears in the above-identified patent and that said Letters Patent is hereby corrected as shown below:

Column 11, structures Ia, Ib, Ic and Id should read as follows:

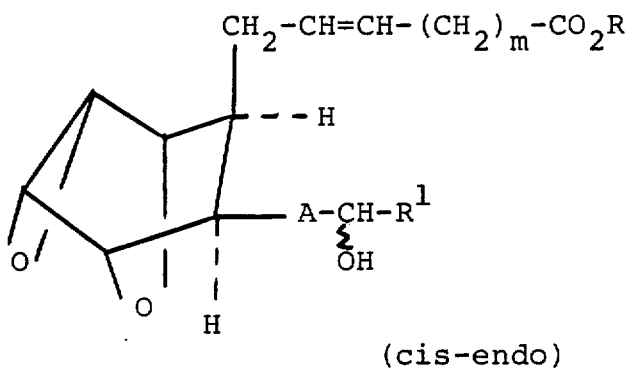

(cis-endo)     Ia

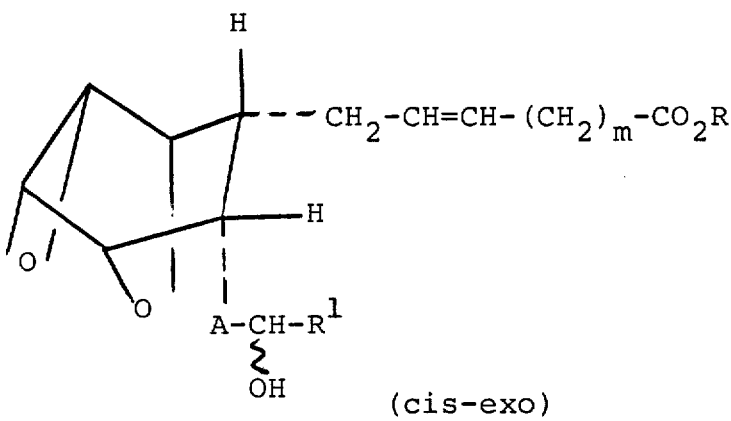

(cis-exo)     Ib

UNITED STATES PATENT AND TRADEMARK OFFICE
CERTIFICATE OF CORRECTION

PATENT NO. : 4,611,005
DATED : September 9, 1986
INVENTOR(S) : Jagabandhu Das

It is certified that error appears in the above-identified patent and that said Letters Patent is hereby corrected as shown below:

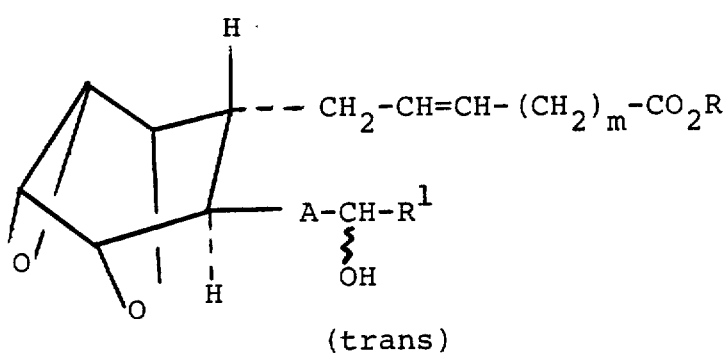

(trans)

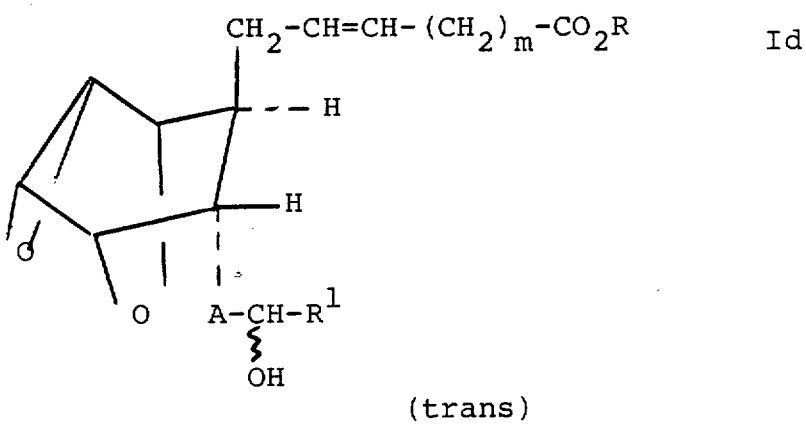

(trans)

UNITED STATES PATENT AND TRADEMARK OFFICE
CERTIFICATE OF CORRECTION

PATENT NO. : 4,611,005

DATED : September 9, 1986

INVENTOR(S) : Jagabandhu Das

It is certified that error appears in the above-identified patent and that said Letters Patent is hereby corrected as shown below:

Column 11, line 49, "( )" should read --($)--.

Column 11, line 64, before "matter" insert --for--.
Column 19, line 67, "so" should read --sodium--.
Column 29, line 15, "1 5" should read --1 to 5--.

Signed and Sealed this

Twenty-third Day of December, 1986

Attest:

DONALD J. QUIGG

*Attesting Officer*     *Commissioner of Patents and Trademarks*